United States Patent
Pflug et al.

(10) Patent No.: US 6,575,752 B1
(45) Date of Patent: Jun. 10, 2003

(54) TOOTH SURFACE TREATMENT COMPOSITION AND METHODS

(75) Inventors: Kai Pflug, Constance (DE); Gordon Brian Blackwell, Constance (DE); Steven R. Jefferies, York, PA (US); Hans Rolf Kase, Constance (DE)

(73) Assignee: Dentsply DeTrey GmbH (DE)

( * ) Notice: Subject to any disclaimer, the term of this patent is extended or adjusted under 35 U.S.C. 154(b) by 0 days.

(21) Appl. No.: 09/569,373

(22) Filed: May 11, 2000

Related U.S. Application Data

(60) Continuation of application No. 09/135,047, filed on Aug. 17, 1998, now abandoned, which is a division of application No. 08/834,614, filed on Apr. 14, 1997, now Pat. No. 6,004,390.

(51) Int. Cl.[7] .............................................. A61C 5/04
(52) U.S. Cl. ................. 433/226; 433/217.1; 433/228.1; 523/116
(58) Field of Search .............................. 433/226, 228.1, 433/217.1, 219; 427/2, 2.26, 2.29; 523/116, 118; 106/35

(56) References Cited

U.S. PATENT DOCUMENTS

| | | | |
|---|---|---|---|
| 4,376,673 A | | 3/1983 | Cheung ....................... 156/662 |
| 4,645,456 A | | 2/1987 | James ....................... 433/217.1 |
| 4,719,149 A | | 1/1988 | Aasen et al. ................ 428/473 |
| 4,810,195 A | | 3/1989 | Asmussen et al. .......... 433/215 |
| 4,880,660 A | * | 11/1989 | Aasen et al. .................. 106/35 |
| 4,952,613 A | | 8/1990 | Hosoda ....................... 523/109 |
| 5,071,637 A | | 12/1991 | Pellico ......................... 424/45 |
| 5,256,447 A | * | 10/1993 | Oxman et al. ............... 156/327 |
| 5,258,067 A | | 11/1993 | Podszun et al. .............. 106/35 |
| 5,290,172 A | | 3/1994 | Sakuma et al. ............. 433/215 |
| 5,385,728 A | | 1/1995 | Suh .............................. 424/54 |
| RE34,937 E | | 5/1995 | Ibsen et al. .................... 106/35 |
| 5,456,602 A | | 10/1995 | Sakuma ...................... 433/215 |
| 5,498,643 A | * | 3/1996 | Antonucci et al. ............. 106/35 |
| 5,554,030 A | | 9/1996 | Ario et al. .................. 433/226 |
| 5,595,487 A | * | 1/1997 | Ario et al. ................. 433/217.1 |
| 5,601,805 A | | 2/1997 | Georgescu .................... 424/55 |
| 5,622,552 A | * | 4/1997 | Arnold ......................... 106/35 |
| 5,708,052 A | * | 1/1998 | Fischer et al. .............. 427/2.26 |
| 5,814,682 A | * | 9/1998 | Rusin et al. ............. 433/228.1 |

FOREIGN PATENT DOCUMENTS

| | | |
|---|---|---|
| DE | 27 39 282 | 2/1978 |
| EP | 0 058 483 | 10/1986 |
| EP | 0 234 934 | 9/1987 |
| EP | 0 329 268 | 8/1989 |
| EP | 0 348 718 | 1/1990 |
| EP | 0 391 629 | 10/1990 |
| EP | 0 609 902 | 8/1994 |
| EP | 0 305 083 | 10/1994 |
| FR | 2561521 | 9/1985 |
| JP | 63-17508 | 10/1988 |
| JP | 63-250310 | 10/1988 |
| WO | 93/12758 | 7/1993 |

OTHER PUBLICATIONS

Staninec et al; The Journal of Prosthetic Dentistry; vol. 55, No. 4 "Bonding of amalgam to tooth structure: Tensile adhesion and microleakage tests"; Apr. 1988; pp. 397–402.

Lacy et al; Quintessence International, vol. 20, No. 7/1989; "The bonded amalgam restoration".

Operative Dentistry, 1989, 124, 142–140; "Inhibition in itro of Caries around Amalgam Restorations by Bonding Amalgam to Tooth Structure".

CRA Newsletter; Feb. 1994.

Aboush et al; Br Dent J 1989; 166: 255; British Dental Journal 1989; "The bonding of glass–ionomer cements to dental amalgam".

Aboush et al; Dental Materials/Apr. 1991; "Bonding of light–curing galss ionomer cement to dental amalgam".

Amar; JADA, vol. 119, Dec. 1989; "Reductio of microleakage around new amalgam restorations".

Mitrosky et al; Quintessence Internation; Sep. 1981; "Cyanoacrylate used as a Bonding Agent Beneath Amalgam and Composite Restorations" pp. 871–874.

Staehle et al; Dtsch Zahnarztl Z 43, 952–957 (1988) Experimentelle Untersuchungen uber die Haftfestigkeit zwischen Amalgam und Zahnhartsubstanzen bei Verwendung von Haftvermittlern.

Buonocore et al; J.D. Res., Dec. 1956; "A report on a resin composition capable of bonding to human dentin surfaces" pp. 846–851.

Buonocore–Quigley . . . vol. 57, Dec. 1958; "Bonding of a synthtic resin material to human dentin: preliminary histological study of the bond area" pp. 807–811.

Ambar et a; J.Dent Res Jul.–Aug. 1974; "Potential Use of Organi Polymphosphonates as Adhesives in the Restoration of Teeth"; pp. 879–888.

Faley et al; J. Dent Res, vol. 56, No. 8, Aug. 1977; "Improved Adhesion of Acrylic Restorative Materials to Dental Enamel by Precoating with Monomers Containing Phosphonate Groups" pp. 943–952.

* cited by examiner

*Primary Examiner*—Pedro Philogene
(74) *Attorney, Agent, or Firm*—Douglas J. Hura; James B. Bieber

(57) ABSTRACT

A tooth surface treatment composition includes an acidic component which is at least one water-soluble acid in an aqueous solution, such that when the composition is applied to the tooth surface and not subsequently washed, it will increase the adhesiveness of the tooth structure. A method of treating a tooth structure includes contacting the tooth structure with such a composition.

9 Claims, No Drawings

TOOTH SURFACE TREATMENT COMPOSITION AND METHODS

This is a continuation of application Ser. No. 09/135,047, filed Aug. 17, 1998, now abandon, which is a divisional application of U.S. patent application Ser. No. 08/834,614 filed, Apr. 14, 1997 now U.S. Pat. No. 6,004,390.

TECHNICAL FIELD

Please amend the specification as follows: On page 12, in the first full paragraph on the page beginning with the phrase "from the results reported above", in the seventh line in that paragraph, immediately following the phrase "some only work well on", delete the word "enamel" and substitute the word therefore "dentin", The present invention relates to tooth surface treatment composition and method. More particularly, the composition includes at least one water soluble acid in an aqueous solution, which may also contain tooth structure priming materials. A method according to the invention includes applying the composition to a tooth structure and subsequently applying dental adhesives and/or restoratives without the need to wash the composition from the tooth structure.

BACKGROUND OF THE INVENTION

In tooth restoration the bonding strength of restorative dental materials to tooth structure including enamel and dentin, is of great importance. Insufficient bonding strength can cause loss of the restoration or formation of marginal gaps generating recurrent caries.

To achieve sufficient bonding strength, a tooth surface treatment is normally required. Phosphoric acid in concentrations of about 36% is widely used as demineralizes enamel prisms, thus promoting a mechanical anchor effect for the resin.

Using phosphoric acid as an etchant, sufficient bonding strength can be reached in combination with a suitable dental adhesive composition. However, the use of phosphoric acid has disadvantages from a use and application point of view. Most notably, it must be washed off after application, requiring the time-consuming procedure of application, washing and drying. Also, as it is completely removed after etching, it does not have any priming effect on the tooth surface.

A need exists therefore, for a material which will cleanse and condition a tooth structure and which does not need to be washed off of the structure before a dental restorative is applied. A need also exists for such a material which will not only cleanse and condition the tooth structure, but which will also prime it to receive the restorative. A further need is to provide this tooth surface treatment composition as a single component.

OBJECTS OF THE INVENTION

It is the object of the invention to provide a tooth surface treatment composition.

It is another object of the invention to provide such a material which will cleanse the tooth structure.

It is an object of the invention to provide such a material which will also condition the tooth structure to receive a dental restorative.

It is a still further object of the invention to provide such a material which will also prime the tooth structure to receive a dental restorative.

It is another object of the invention to provide a method of cleansing, conditioning and/or priming a tooth structure.

It is still another object of the invention to provide such a method which does not require that the primer/cleanser/conditioner be washed off of the tooth structure prior to a dental restorative being applied.

It is yet another object of the invention that this tooth surface treatment composite be provided as a single component so that mixing of two or more components is not necessary.

These and other objects of the invention, which shall become apparent from the description to follow, are achieved by the invention as hereinafter described and claimed.

SUMMARY OF THE INVENTION

In general, a tooth surface treatment composition according to the invention comprises an acidic component which comprises at least one water-soluble acid in an aqueous solution, such that when the composition is applied to the tooth surface it will increase the adhesiveness of the tooth structure without the need for washing the composition from the tooth surface. This composition can be provided as a single component material for ease of application and storage.

There is also provided according to the invention a method of treating a tooth structure which comprises the steps of: (a) physically contacting the tooth structure with a conditioner comprising at least one water-soluble acid in an aqueous solution; and, (b) at least partially drying the conditioner. The conditioner adheres to the tooth structure without the need for a washing step intermediate steps (a) and (b).

A method of adhesively restoring a tooth structure according to the present invention comprising the steps of: (a) physically contacting the tooth structure with a conditioner comprising at least one water-soluble acid in an aqueous solution; (b) at least partially drying the conditioner; (c) applying a dental adhesive to the tooth structure; and, (d) applying a dental restorative material to the tooth structure. The dental adhesive bonds to the tooth structure without the need for the conditioner to be first washed from the tooth structure.

DETAILED DESCRIPTION

The tooth surface treatment composition according to the present invention includes an aqueous solution of one or more water-soluble acids, preferably with an overall acid content of about 1 to about 50 weight percent, more preferably about 1 to 20 weight percent. The composition when applied to a tooth structure will enhance the adhesiveness of the structure without the need for washing. In addition, the composition may also contain additional components enhancing the priming, cleansing or conditioning effect of the composition, and as will be more fully explored hereinbelow.

The term "dental adhesive" and the like as used herein and as described in step (c) above, can apply to a wide range of materials which can effect a bond to both conditioned enamel and dentin. At a minimum, the dental adhesive contains a polymerizable resin component or components necessary to effect the initiation and acceleration of polymerization by visible or actinic light or by chemical means, and a polymerizable monomer or monomers containing an ionic functionality such as a phosphate or caboxylic (COOH) acid function. Preferably, this dental adhesive may be in the form of a self-priming adhesive which further contains a volatile solvent such as acetone, ethanol and mixtures thereof. Water may also be used as a solvent. The dental adhesive may comprise a one-component material, or may alternatively have two components. The second component of the dental adhesive may contain initiators and/or accelerators, to facilitate chemical curing alone or combined with curing upon exposure to actinic light to provide a dual-cure mode of polymerization. Examples of substances which facilitate self-curing of dental adhesives include for example, BPO, DHEPT and aromatic sulfinic acid salts.

Acids useful for the purpose of the invention are compounds which exhibit acidity when dissolved in water. Examples of acids include phosphoric acid, nitric acid, tartaric acid, maleic acid, itaconic acid, 5-sulfosalicylic acid, propionic acid, citric acid, hydrochloric acid, oxalic acid, latic acid. Especially preferred acids are maleic acid, itaconic acid, nitric acid and phosphoric acid, more particularly combinations of maleic acid and itaconic acid. One preferred composition contains about 3 to about 10 weight percent maleic acid and from 0 to about 9 weight percent (more preferably from about 2 to about 7 percent by weight) itaconic acid. Unless otherwise noted, all "percent", "%" and similar designations as used herein, refer to weight percent.

The tooth surface treatment composition may contain additional components enhancing the priming, cleansing or conditioning effect of the composition. Examples for substances with such effects are chemicals containing polymerizable double bonds such as those of methacrylic or similar groups; additional acids with good or limited solubility in water, surfactants and the like. More specifically, examples of useful priming components include alpa-methylene-gamma-butyrolactone, hydroxyethyl metacrylate, itaconic acid, ethyltriglycol methacrylate and 2-(methacryloyloxy) ethyl phosphate and the like.

The amount of water used is 100 weight percent less the total proportion of other contents, preferably 50 to 99 weight percent, more preferably, 80 to 98 weight percent. Distilled or deionized water is preferred, as it does not contain impurities potentially harmful to the adhesive properties of the solution. The composition may also contain 0 to 2 percent fluoride in the form of sodium fluoride or another fluoride compound.

A water compatible volatile solvent may be added to the composition, such as acetone, ethanol and mixtures thereof. When volatile solvents are used in the composition, the amount of water may be decreased to as low as 2 percent. The composition may also, optionally, contain a hydrophilic resin or monomer, such as for example, hydroxyethyl methacrylate (HEMA).

One preferred composition according to the invention includes from about 3 to about 12 percent by weight of an acidic component, from about 0 to about 10 percent by weight of a priming component, and the remaining amount to 100 percent by weight being water. A preferred acidic component is 5–8 weight percent maleic acid. A preferred priming component is 2–7 percent by weight of itaconic acid.

The aqueous solution of the acids may be applied directly to the wet tooth surface. After a specified time ranging from 5 to 100 seconds, preferably 10 to 40 seconds, the tooth surface is dried. Washing is not required.

After applying the tooth surface treatment composition, a photopolymerizable dental adhesive system may be applied, dried and light cured, followed by application and curing of a dental restorative material. Of course, a chemically cured adhesive may also be employed.

A preferred method of treating a tooth structure includes physically contacting the tooth structure with a conditioner as described above and including a priming component. The method also includes at least partially drying the conditioner from the tooth structure. Drying may be by any conventional means such as by air or forced air. The conditioner adheres to the tooth structure without the need for a washing step intermediate steps (a) and (b).

A method of adhesively restoring a tooth structure according to the present invention includes physically contacting the tooth structure with a conditioner as also described hereinabove, and preferably yet optionally containing the priming component. The conditioner composition is at least partially dried as above, and a dental adhesive is applied to the tooth structure. Following the adhesive a dental restorative material is applied to the tooth structure. The dental adhesive bonds to the tooth structure without the need for the conditioner to be first washed from the tooth structure.

The dental adhesives and restoratives used in the practice of the present invention are those conventional in the art. For example, one useful dental adhesive includes Prime & Bond 2.1 (available from Dentsply International Inc.). Preferred dental adhesives are cure by exposure to light, preferably visible light.

Useful dental restorative materials or cements include amalgam and non-amalgam dental restoratives. Examples of useful non-amalgam materials include compomer restorative, composite resin restorative, glass ionomer-resin restorative, glass ionomer-resin luting cement, resin cement and resin dental sealant. Examples of useful compomers are those having as a principle functional ingredient polymerizable unsaturated monomers of a substituted butane moiety with acid or reactive acid derivative functionality having the general formula $(RO_2C)_x$—$C_4H_6$—$(CO_2R_1)_y$ where R is an acid radical or a reactive acid derivative and R' is a polimerizable unsaturated radical having from about 2 carbon atoms to about 13 carbon atoms and "x" is 2 to 3 and "y" is 1 to 2. A description of such materials is provided in U.S. Pat. No. 5,218,070 which is hereby incorporated by reference for such disclosure. Examples of composite resin restoratives include T?H Spectrum available from Dentsply International Inc. Examples of glass ionomer-resin restoratives include Dyract available from Dentsply International Inc. Examples of glass ionomer-resin luting cements include Dyract CEM available from Dentsply International Inc. Examples of a resin cement include DICOR MGC Luting Cement and EnForce Resin Cement, both available from Dentsply International Inc. Examples of a resin dental sealant include Delton available from Dentsply International Inc.

One preferred dental restorative material is a two-component composite resin which is self-curable by chemical means, available from Dentsply International Inc. as ADAPTIC.

EXAMPLES

The following examples are given to demonstrate the practice of the present invention. It is understood, however, that the invention is not limited by these examples.

Using tooth surface treatment compositions prepared from combinations of various acids as discussed above and deionized water, shear bond tests were carried out to test adhesion to enamel and dentin.

The Prime & Bond 2.0 primer (Dentsply) was used as primer, and TPH Spectrum (Dentsply) was used as light-cure type composite resin. Bond strength was determined by the shear bond strength of the composite resin in relation to enamel and dentin. Human molars were used.

For purposes of enamel bond tests, the enamel surface of 6 human molars was polished with carborund (SiC). This fresh, dry enamel surface was treated with the respective tooth surface treating agent for 20 seconds, followed by compressed air drying. Hereafter, Prime & Bond 2.0 was applied and 20 seconds later, compressed air drying was effected. This coat was light-cured for 20 seconds, using a Spectrum curing light (Dentsply). Subsequently, a plastic mold with an inner diameter of 5 mm and a height of 2 mm was fixed to the surface and TPH Spectrum was filled into the interior of the mold. The surface was subjected to visible light irradiation by the Spectrum curing light via the mold for 40 seconds. After light-curing, the teeth were stored at 37° C. for 24 hours then thermocycled 500 times (20 seconds at 5° C., 20 seconds at 55° C.), embedded in gypsum and tested with a Zwick Z010/TN2A tabletop, universal testing machine at a speed for 1 mm/min (millimeter/minute)

Fur purposes of dentin bond tests, the dentin surfaces of 6 human molars were exposed with a diamond saw and ground with #500 sandpaper. This fresh dentin surface was treated with the respective tooth surface treating agent for 20 seconds, followed by careful drying with a paper towel. This drying leaves a dry-looking surface but is not too harsh. Thereafter, Prime & Bond 2.0 was applied and, 20 seconds later, compressed or forced air drying was effected. This coat was light-cured for 20 seconds, using a Spectrum curing light (Dentsply). Subsequently, a plastic mold with an inner diameter of 5 mm and a height of 2 mm was fixed to the surface and TPH Spectrum was filled into the interior of the mold. The surface was subjected to visible light irradiation by the Spectrum curing light via the mold for 40 seconds. After light-curing the teeth were stored at 37° C. for 24 hours, then thermocycled 500 times (20 seconds at 5° C., 20 seconds at 55° C.), embedded in gypsum and tested with a Zwick Z010/1N2A tabletop universal testing machine at a speed of 1 mm/min.

Results of these tests, and the materials tested are reported in Table 1. Examples 1–29 are reported. Table 1: Adhesion using various tooth surface treatment compositions

| Example | treating agent (in water) | Adhesion (MPa) Enamel | Dentin |
| --- | --- | --- | --- |
| 1 | 2.5% 5-sulfosallcylic acid | 12.2(22) | 17.4(29) |
| 2 | 5% 5-sulfosallcylic acid | 14.3(28) | 9.1(11) |
| 3 | 10% 5-sulfosallcylic acid | 14.3(25) | 1.9(39) |
| 4 | 30% M | 12.9(18) | 22.1(17) |
| 5 | 6% M | 16.6(11) | 14.6(19) |
| 6 | 10% M | 16.9(24) | 16.2(34) |
| 7 | 3% I | 8.4(34) | 27.1(24) |
| 8 | 6% I | 11.8(22) | 22.4(20) |
| 9 | 10% I | 12.1(17) | 21.3(24) |
| 10 | 3% M, 3% 5-sulfosalicylic acid | 16.6(17) | 13.3(39) |
| 11 | 3% I, 2% 5-sulfosalicylic acid | 11.3(21) | 18.8(24) |
| 12 | 3% I, 3% phosphoric acid | 16.3(19) | 15.6(40) |
| 13 | 3% I, 3% nitric acid | 15.7(20) | 13.9(49) |
| 14 | 3% I, 3% hydrochloric acid | 15.0(20) | 5.5(51) |
| 15 | 3% I, 3% citric acid | 10.6(29) | 20.8(20) |
| 16 | 3% I, tartaric acid | 4.1(74) | 3.0(61) |
| 17 | 3% I, 3% lactic acid | 10.1(37) | 22.0(20) |
| 18 | 3% I, propionic acid | 10.5(34) | 19.9(27) |
| 19 | 3% M, 3% I | 16.0(35) | 24.7(19) |
| 20 | 4% M, 2% I | 15.8(17) | 22.4(15) |
| 21 | 4% M, 4% I | 17.2(6) | 21.7(16) |
| 22 | 5% M, 5% I | 19.0(10) | 19.1(12) |
| 23 | 6% M, 6% I | 16.9(23) | 21.1(17) |
| 24 | 8% M, 8% I | 16.2(29) | 18.1(32) |
| 25 | 5% M, 5% I | 15.5(11) | 19.6(19) |
| 26 | 5% M, 5% I, 5% ethyltriglycol methacrylate | 18.6(18) | 19.3(17) |
| 27 | 5% M, 5% I, 5% hydroxyethyl methacrylate | 18.0(21) (3.0 (23)) | 19.0(29) |
| 28 | 5% M, 5% I, 5% dimethylaminoethylmethacrylate | 15.1(14) | 23.7(26) |
| 29 | 5% M, 5% I, 0.5% NaI | 15.5(11) | 19.6(19) |

In brackets: coefficient of variation
Abbreviations: M maleic acid, I itaconic acid

TABLE 2

Comparative Examples (Adhesion using conventional etching technique with phosphoric acid)

| Comp. Example | Method | Adhesion (MPa) Enamel | Dentin |
| --- | --- | --- | --- |
| 1 | etching with phosphoric acid 36%, washing, 2 coats of Prime & Bond 2.0 | 11.8(21) | 14.8(23) |
| 2 | etching with phosphoric acid 36%. no washing, 2 coats of Prime & Bond 2.0 | <2.0 | <2.0 |
| 3 | no etching, 2 coats of Prime & Bond 2.0 | 3.8(52) | 18.8(19) |

From the results reported above, it is apparent that the tooth surface treating agents of this invention can impart high bond effect to the enamel and dentin through simultaneous treatment thereof if the right combination of acids is chosen. Some compositions give low adhesion on dentin and enamel (example 16), some only work well on enamel (example 3, 14), some only work well on enamel (example 4, 7, 8, 15, 17, 18), but some compositions give high adhesion both to enamel and to dentin (examples 5, 6, 12, 13, 19–25). Especially preferred are combinations of maleic and itaconic acid.

For example, the composition of example 22 yields adhesion values to enamel and dentin that are as high as those achieved with the conventional etching technique used in comparative example 1. This shows that the inventive composition and method as described herein, achieve high adhesion values. Further, the time-consuming step of washing the tooth structure when employing heretofore conventional materials, most notably phosphoric acid etching techniques, is avoided. The somewhat stronger etching achieved by the phosphoric acid is compensated for by the additional priming effect of the described dental compositions. Additional substances may be added to enhance this priming effect (examples 26, 27). Also, inclusion of fluoride is possible (example 29).

In another series of experiments, bond strengths of Spectrum TPH to tooth structures pretreated with the inventive material were investigated. The investigations and specific tooth structures are reported hereinbelow.

Dentin

Clean dentinal surfaces were treated with an inventive composition comprising 5 wt. percent maleic acid and 5 wt.

percent itaconic acid (hereinafter designated K-0100) for 20 seconds. The surface was blot dried lightly with tissue paper but not rinsed. Prime & Bond 2.1 was applied and left undisturbed for 20 seconds. Excess solvent was removed by air-drying. Prime & Bond 2.1 was light-cured for 20 seconds. Spectrum TPH was applied and light-cured. Specimens were stored in water for 24 hours and debonded.

As a control series, etching with DeTrey Conditioner 36 (36% phosphoric acid gel) was employed. Clean dentinal surfaces were treated with DeTrey Conditioner 36 for 20 seconds. The surface was rinsed thoroughly and blot dried lightly with tissue paper. Prime & Bond 2.1 was applied and left undisturbed for 20 seconds. Excess solvent was removed by air-drying. Prime & Bond 2.1 was light-cured for 10 seconds. A second layer of Prime & Bond 2.1 was applied. Excess solvent was removed by air-drying. Prime & Bond 2.1 was light-cured for 10 seconds. Spectrum TPH was applied and light-cured. Specimens were stored in water for 24 hours and debonded by physical scraping with a hard-edged instrument.

Enamel

Clean enamel surfaces were treated with K-0100 for 20 seconds. The surface was air-dried but not rinsed. Prime & Bond 2.1 was applied and left undisturbed for 20 seconds. Excess solvent was removed by air-drying. Prime & Bond 2.1 was light-cured for 20 seconds. Spectrum TPH was applied and light-cured. Specimens were stored in water for 24 hours and debonded.

As control series, etching with DeTrey Conditioner 36 (36% phosphoric acid gel) was employed. Clean enamel surfaces were treated with DeTrey Conditioner 36 for 20 seconds. The surface was rinsed thoroughly and air-dried. Prime & Bond 2.1 was applied and left undisturbed for 20 seconds. Excess solvent was removed by air-drying. Prime & Bond 2.1 was light-cured for 10 seconds. A second layer of Prime & Bond 2.1 was applied. Excess solvent was removed by air-drying. Prime & Bond 2.1 was light-cured for 10 seconds. Spectrum TPH was applied and light-cured. Specimens were stored in water for 24 hours and debonded.

Table 3 below shows the results obtained.

K-0100. On ground enamel, the result is similar for these treatments at 40 and 60 seconds; at 20 seconds, demineralization with K-0100 is slightly less. On unground enamel, the phosphoric acid effect is significantly greater at all times with increasing but less dramatic dissolution of enamel with K-0100.

In summary, changes on dentin are comparable while on enamel, inventive K-0100 causes less changes on the surface than when employing conventional acid etching techniques. Further, the inventive materials do not influence bond strengths.

Phosphoric acid etching leads to phosphates precipitating on the tooth surface. The phosphates have to be removed thoroughly as they interfere with subsequent bonding steps. This cleaning step is not necessary with the inventive materials such as K-0100 as they not have a detrimental effect upon the subsequent bonding steps. Further, the acids in the present invention are milder than phosphoric acid. This reduces the chance of irritations of the mucosa at unintentional contacts.

The foregoing description illustrates preferred embodiments of the invention. However, concepts employed may, based upon such description, be employed in other embodiments without departing from the scope of the invention. Accordingly, the following claims are intended to recite the invention broadly, as well as in the specific forms herein.

What is claimed is:

1. A method of treating a tooth structure comprising the steps of:
    (a) physically contacting the tooth structure with a tooth surface treatment solution comprising maleic acid, itaconic acid and optionally at least one water-soluble acid in an aqueous solution; and,
    (b) at least partially drying said solution;
    wherein said tooth surface treatment solution achieves retentively significant levels of adhesion to the tooth structure without the need for a washing step intermediate steps (a) and (b).

2. A method as in claim 1, wherein said step of physically contacting the tooth structure with a tooth surface treatment solution comprises physically contacting the tooth structure with a composition comprising at least one other water-

TABLE 3

| SYSTEM | K-0100/Dentin | $H_2PO_4$/Dentin | K-0100/Enamel | $H_2PO_4$/Enamel |
|---|---|---|---|---|
| Adhesive (first coat) | Prime & Bond 2.1 | Prime & Bond 2.1 | Prime & Bond 2.1 | Prime & Bond 2.1 |
| Light-curing | 20 seconds | 10 seconds | 20 seconds | 10 seconds |
| Adhesive (second coat) | no | Prime & Bond 2.1 | no | Prime & Bond 2.1 |
| Light-curing | NA | 10 seconds | NA | 10 seconds |
| Bond Strength (MPa ± S.D.) | 19.16 ± 3.16 | 21.19 ± 3.02 | 28.14 ± 2.14 | 29.92 ± 3.04 |
| Cohesive Failures (%) | 20 | 20 | 100 | 90 |

These results show that within experimental error, identical adhesion values can be achieved using tooth pretreatment with inventive K-0100 as with conventional acid etching.

Effects of K-0100 on Tooth Surface

The structural changes on dentin and enamel surfaces after use of K-0100 were tested and compared with the structural changes occurring after phosphoric acid etching. On dentin, comparable structural changes could be observed at 20, 40 and 60 seconds application of phosphoric acid and soluble acid selected from the group consisting of phosphoric acid, nitric acid, tartaric acid, 5-sulfosalicylic acid, propionic acid, citric acid, hydrochloric acid, oxalic acid and lactic acid.

3. A method of adhesively restoring a tooth structure comprising the steps of:
    (a) physically contacting the tooth structure with a tooth surface treatment solution comprising maleic acid, itaconic acid and optionally comprising at least one water-soluble acid in an aqueous solution;
    (b) at least partially drying said tooth surface treatment solution;

(c) applying a dental adhesive to the tooth structure; and, (d) applying a dental restorative material to the tooth structure;

wherein said dental adhesive bonds to the tooth structure without the need for said tooth surface treatment solution to be first washed from the tooth structure.

4. A method as in claim 3, wherein said step of physically contacting the tooth structure with a tooth surface treatment solution comprises physically contacting the tooth structure with a composition comprising at least one other water-soluble acid selected from the group consisting of phosphoric acid, nitric acid, tartaric acid, 5-sulfosalicylic acid, propionic acid, citric acid, hydrochloric acid, oxalic acid and lactic acid.

5. A method as in claim 3, wherein said step of applying a dental restorative material comprises applying a dental cement.

6. A method as in claim 3, wherein said step of applying a dental restorative material comprises applying a dental restorative material selected from the group consisting of an amalgam and a non-amalgam dental restorative.

7. A method as in claim 6, wherein said step of applying a non-amalgam material comprises the step of applying a material selected from the group consisting of compomer restorative, composite resin restorative, glass ionomer-resin restorative, glass ionomer-resin luting cement, resin cement and resin dental sealant.

8. A method as in claim 3, comprising the further step of curing said dental adhesive by exposure to light.

9. A method as in claim 3, wherein said step of applying a dental restorative material comprises applying a two-component dental adhesive which is self-curable by chemical means.

* * * * *